(12) United States Patent
Ma et al.

(10) Patent No.: US 12,228,690 B2
(45) Date of Patent: Feb. 18, 2025

(54) DETECTION COLLIMATION UNIT, DETECTION APPARATUS AND SPECT IMAGING SYSTEM

(71) Applicant: Tsinghua University, Beijing (CN)

(72) Inventors: Tianyu Ma, Beijing (CN); Yaqiang Liu, Beijing (CN); Xuewu Wang, Beijing (CN); Zhong Wang, Beijing (CN)

(73) Assignee: Tsinghua University, Beijing (CN)

( * ) Notice: Subject to any disclaimer, the term of this patent is extended or adjusted under 35 U.S.C. 154(b) by 146 days.

(21) Appl. No.: 18/041,439

(22) PCT Filed: Aug. 12, 2021

(86) PCT No.: PCT/CN2021/112298
§ 371 (c)(1),
(2) Date: Feb. 13, 2023

(87) PCT Pub. No.: WO2022/037473
PCT Pub. Date: Feb. 24, 2022

(65) Prior Publication Data
US 2023/0296795 A1    Sep. 21, 2023

(30) Foreign Application Priority Data
Aug. 19, 2020    (CN) .......................... 202010840410.2

(51) Int. Cl.
*G01T 1/00*    (2006.01)
*G01T 1/164*    (2006.01)
(Continued)

(52) U.S. Cl.
CPC .......... *G01T 1/1642* (2013.01); *G01T 1/2992* (2013.01); *G21K 1/025* (2013.01)

(58) Field of Classification Search
CPC ............... G01T 1/1642; G01T 1/20186; G01T 1/2992; G01T 1/2023
See application file for complete search history.

(56) References Cited

U.S. PATENT DOCUMENTS

| | | | |
|---|---|---|---|
| 4,234,792 A | 11/1980 | DeCou et al. | |
| 4,303,860 A | 12/1981 | Bjorkholm et al. | |
| (Continued) | | | |

FOREIGN PATENT DOCUMENTS

| | | |
|---|---|---|
| CA | 1 139 897 A | 1/1983 |
| CN | 108139491 A | 6/2018 |
| (Continued) | | |

OTHER PUBLICATIONS

Notice of Reasons for Refusal, for Japanese Patent Application No. 2023-509847, dated Mar. 19, 2024, 6 pages.
(Continued)

*Primary Examiner* — Dani Fox
(74) *Attorney, Agent, or Firm* — Westman, Champlin & Kochler, P.A.

(57) ABSTRACT

Disclosed are a detection collimation unit, a detection apparatus and a SPECT imaging system. The detection collimation unit includes: a scintillation crystal array configured to receive a gamma photon emitted by a radioactive source in a detected object; and a number of photoelectric devices configured to receive the gamma photon and converting the gamma photon into a digital signal. The scintillation crystal array includes a number of scintillation crystals. The number of scintillation crystals are arranged substantially in parallel and are spaced from each other. Each scintillation crystal has a side face configured to receive a ray emitted by the radioactive source and an end face. The number of photoelectric devices are coupled to the end faces of the number of scintillation crystals.

11 Claims, 6 Drawing Sheets

(51) Int. Cl.
*G01T 1/29* (2006.01)
*G21K 1/02* (2006.01)

(56) References Cited

U.S. PATENT DOCUMENTS

| | | |
|---|---|---|
| 4,415,808 A | 11/1983 | Cusano et al. |
| 8,115,174 B2 | 2/2012 | Nelson |
| 8,212,220 B2 | 7/2012 | Lerch et al. |
| 10,213,173 B2 * | 2/2019 | Wieczorek ............ A61B 6/4258 |
| 10,371,830 B2 | 8/2019 | Jacobs et al. |
| 10,448,909 B2 | 10/2019 | Wieczorek et al. |
| 2009/0134334 A1 | 5/2009 | Nelson |
| 2010/0090115 A1 | 4/2010 | Lerch et al. |
| 2014/0343412 A1 | 11/2014 | Wieczorek et al. |
| 2018/0275289 A1 | 9/2018 | Jacobs et al. |
| 2019/0090827 A1 | 3/2019 | Wieczorek et al. |
| 2022/0066056 A1 | 3/2022 | Ma et al. |

FOREIGN PATENT DOCUMENTS

| | | |
|---|---|---|
| CN | 108697398 A | 10/2018 |
| CN | 111329500 A | 6/2020 |
| JP | 2017003392 A | 1/2017 |
| JP | 2018-537658 A | 12/2018 |
| WO | 2008095257 A1 | 8/2008 |
| WO | 2019/042797 A1 | 3/2019 |
| WO | 2019135676 A1 | 7/2019 |

OTHER PUBLICATIONS

Examination report No. 2 for standard patent application, for Australian Patent Application No. 2021329704, dated Apr. 10, 2024, 4 pages.
International Search Report and Written Opinion for International Application No. PCT/CN2021/112298, dated Oct. 26, 2021, 8 pages.
Examination report No. 1 for standard patent application, for Australian Patent Application No. 2021329704, dated Nov. 15, 2023, 3 pages.
Notice of Reasons for Refusal, for Japanese Patent Application No. 2023-509847, dated Nov. 14, 2023, 8 pages.
Extended European search report for European patent application No. 21857568.6, dated Jul. 17, 2024, 9 pages.
Examiner's Report for Canadian patent application No. 3,189,947, dated Aug. 9, 2024, 4 pages.
The Office Action for Korean Patent Application No. 10-2023-7004481, dated Nov. 25, 2024, 30 pages.
Translation of the Office Action for Korean Patent Application No. 10-2023-7004481, dated Nov. 25, 2024, 7 pages.
Translation of the First Office Action for Chinese Patent Application No. 202010840410.2, dated Dec. 19, 2024, 13 pages.

* cited by examiner

DETECTION COLLIMATION UNIT, DETECTION APPARATUS AND SPECT IMAGING SYSTEM

CROSS REFERENCE TO RELATED APPLICATION(S)

This application is a Section 371 National Stage Application of International Application No. PCT/CN2021/112298, filed on Aug. 12, 2021, entitled "DETECTION COLLIMATION UNIT, DETECTION APPARATUS AND SPECT IMAGING SYSTEM", which published as WIPO Publication No. WO 2022/037473 A1, on Feb. 24, 2022, not in English, which claims priority to Chinese Patent Application No. 202010840410.2, filed on Aug. 19, 2020, the contents of which are incorporated herein by reference in their entireties.

TECHNICAL FIELD

The present disclosure relates to a field of a nuclear medical imaging technology, and in particular, to a detection collimation unit, a detection apparatus including a detection collimation unit and a SPECT imaging system.

BACKGROUND

A SPECT (Single photon emission computed tomography) device for a nuclear medical imaging diagnosis needs to include at least two components to achieve a SPECT imaging function. One of the two components is a detector component, which receives a plurality of gamma photons emitted from a detected object at different times one by one, converts a time information, an energy information, and a position information of each photon acting on a detector into an electrical signal and digitally inputs the electrical signal to a computer. The other one of the two components is a collimator component, which is generally located between the detected object and the detector component, and absorbs photons emitted from certain specific directions in the detected object, so that the photons arriving at the detector component may not be detected when the photons come from the above-mentioned directions, or a probability that the photons arriving at the detector component come from certain specific directions is significantly different from a probability that the photons come from other directions. Thus, the photons received by the detector component also include an incident direction information. All detection units on the detector component receive a certain number of gamma photons one by one within a period of imaging time, and the gamma photons are sum up to obtain the number of gamma photons on each detection unit. An information related to the number of the gamma photons on each detection unit is input into an image reconstruction algorithm component in the computer. In the image reconstruction algorithm, a probability that a gamma photon emitted by each point in an imaging space is received by each detection unit of the detector component is recorded in a form of system transmission matrix calculated by a geometric model formula or discretized measurement in advance. The image reconstruction algorithm may solve a radioactive source intensity distribution information in the detected object through a mathematical operation by using the above-mentioned probability information and the input gamma photon information, and form a digital image to be displayed in a display unit.

Different from a transmissive CT imaging system (a radioactive source of the transmissive CT imaging system is located outside a human body, and an X-ray generating apparatus, such as an X-ray bulb, etc., is usually used as the radioactive source, so a ray passing through the human body itself has a directivity), a radioactive source of the SPECT imaging system is a radioactive tracer introduced into the human body by an injection, an oral administration or inhalation method, and the tracer emits the gamma photon in an isotropic manner, so that the gamma photon detected by the SPECT system does not carry a direction information. Therefore, a conventional SPECT system needs to use an absorption collimator made of a heavy metal, which only allows a gamma photon from a specific direction to enter the detector and absorb gamma photons from other directions, so that the gamma photon received by the detector may carry the direction information. However, in the SPECT system, a design of the collimator component faces a dilemma: on the one hand, if the collimator component absorbs photons from a majority of directions and allows only photons from a few directions to enter the detector, each photon arriving at the detector may carry a more effective direction information, which may be beneficial to improve a spatial resolution of the imaging system; however, the number of photons emitted by the radioactive source in unit time follows a Poisson statistical distribution, resulting in a relative fluctuation in the number of photons acquired on the detection unit, and the relative fluctuation in a form of standard deviation is inversely proportional to a square root value of the number of photons acquired. Therefore, when a collimator is designed, a consideration is also required to allow more photons to enter the detector, that is, to improve a detection efficiency of the imaging system, so as to increase the number of gamma photons received on each detection unit, and correspondingly reduce a relative statistical fluctuation. In this way, however, the collimator needs to allow the photons from more directions to enter the detector, thereby reducing an effectiveness of the direction information carried by each photon received by the detector, that is, reducing the spatial resolution of the imaging system.

For a traditional heavy metal collimator, it is tried to reduce a size of an opening and a spacing between openings in an incident direction of the gamma photon, in order to ensure the spatial resolution of the SPECT system. However, this may often cause a situation that a large number of gamma photons are attenuated and absorbed by the collimator and thus may not be detected by the detector, which may result in a loss of a large number of photons and seriously affect a detection efficiency of the SPECT device.

Therefore, the spatial resolution and the detection efficiency of the SPECT system cannot be both improved due to the existence of a heavy metal collimator component.

On the other hand, in order to make the gamma photon pass through the heavy metal collimator component, a plurality of parallel straight holes or conical pinholes need to be processed on the heavy metal collimator component. A shape parameter of the holes may have a great impact on a performance of the SPECT system, and therefore a processing size needs to be precisely controlled, and the metal processing is highly difficult.

SUMMARY

In order to solve at least one of the above-mentioned problems, an object of the present disclosure is to provide a detection collimation unit, a detection apparatus and a SPECT imaging system that may improve a spatial resolution, and/or improve a detection efficiency, and/or reduce a difficulty of metal processing.

According to a first aspect of the present disclosure, a detection collimation unit is provided, including:

a scintillation crystal array configured to receive a gamma photon emitted by a radioactive source in a detected object; and a number of photoelectric devices configured to receive the gamma photon and converting the gamma photon into a digital signal;

wherein the scintillation crystal array includes a number of scintillation crystals, the number of scintillation crystals are arranged substantially in parallel and are spaced from each other, and each scintillation crystal has a side face configured to receive a ray emitted by the radioactive source and an end face; and wherein the number of photoelectric devices are coupled to the end faces of the number of scintillation crystals.

Preferably, the scintillation crystal array is a two-dimensional array, and the scintillation crystal array includes a number of scintillation crystals arranged in an incident direction of a gamma ray emitted by the radioactive source, and a number of scintillation crystals arranged in a direction perpendicular to the incident direction of the gamma ray emitted by the radioactive source.

Preferably, the scintillation crystal includes at least one independent scintillation crystal strip and/or a plurality of scintillation crystal strips spliced together.

Preferably, at least one end face of the scintillation crystal strip is coupled with a photoelectric device.

Preferably, in the scintillation crystal array, a filler is provided between the scintillation crystals spaced from each other, and a material of the filler includes at least one of resin, polyethylene plastic, organic glass and heavy metal.

According to a second aspect of the present disclosure, a detection apparatus is provided, including a number of detection collimation units according to any one of the above-mentioned solutions.

Preferably, the number of detection collimation units are fixedly connected to form a detection collimation unit layer which is distributed around the detected object in a shape of any of a circle, a polygon, an arc and a partial polygon.

Preferably, the detection apparatus includes a number of detection collimation unit layers which are arranged in an incident direction of a gamma ray emitted by a radioactive source and are spaced from each other, and the number of detection collimation unit layers are staggered, so that at least one scintillation crystal is contained in the detection collimation unit of the last detection collimation unit layer, and a gamma photon emitted from a point of an imaging field of view does not pass through any photoelectric device or circuit board material in a transmission path along which the gamma photon is incident and reaches the scintillation crystal of the last detection collimation unit layer.

According to a third aspect of the present disclosure, a SPECT imaging system is provided, including the detection apparatus according to any of the above-mentioned solutions, a data processing unit, an image reconstruction unit and an image display unit;

wherein the data processing unit is configured to receive and process a digital signal output by the detection apparatus, so as to obtain an incident information of each incident gamma photon; and wherein the image reconstruction unit is configured to receive and process the incident information of a plurality of incident gamma photons output by the data processing unit, so as to obtain a distribution information of a radioactive source in a detected object and form a digital image; and wherein the image display unit is configured to display the digital image to provide an information required for a clinical diagnosis.

Preferably, each detection collimation unit layer of the detection apparatus is selectively rotatable around the detected object.

Preferably, the SPECT imaging system includes at least two detection apparatuses which are arranged in an incident direction of a gamma ray emitted by the radioactive source and are spaced from each other, and in the incident direction of the gamma ray emitted by the radioactive source, a far-end detection apparatus far away from the detected object is configured to receive a gamma photon. which is emitted by the radioactive source in the detected object and passes through one or more near-end detection apparatuses, and convert the gamma photon into the digital signal.

Preferably, a relative position of each detection apparatus in the SPECT imaging system, a spacing between two adjacent detection apparatuses, a number of scintillation crystal strips in each detection collimation unit, a size of the scintillation crystal strip, and an arrangement mode parameter of the scintillation crystal strip are selected according to a spatial resolution and an image signal-to-noise ratio required by the SPECT imaging system.

Preferably, a heavy metal collimator with an opening is provided between a first detection apparatus close to the detected object and the detected object, and/or between two adjacent detection apparatuses in an incident direction of a gamma ray emitted by the radioactive source, and/or, between the detection collimation unit layers of each detection apparatus.

Further, a photon transmittance of the heavy metal collimator is greater than 1%.

Compared with the prior art, the present disclosure achieves the following technical effects:

The present disclosure provides a detection collimation unit. The detection collimation unit includes the plurality of photoelectric devices and the scintillation crystal array, which includes the plurality of scintillation crystals arranged substantially in parallel and spaced from each other. The plurality of photoelectric devices are coupled to the end faces of the plurality of scintillation crystals, so that the gamma photon emitted by the radioactive source in the detected object, when being incident from the side face of the scintillation crystal, does not need to pass through the photoelectric device (that is, the photoelectric device is substantially parallel to the incident direction of the gamma photon emitted by the radioactive source in the detected object). In this way, an effect of gamma ray direction alignment and a goal of photon detection is achieved without affecting an image quality. Furthermore, compared with an existing imaging system in which a heavy metal collimator that does not allow a ray to pass therethrough is used, the detection collimation unit of the present disclosure may avoid a loss of the gamma photon and greatly improve a detection efficiency of the gamma photon, without affecting an imaging quality of the SPECT imaging system. At the same time, a difficulty in processing g a plurality of small parallel holes or pinholes in the heavy metal collimator may be avoided, and the processing may be simplified.

In addition, the present disclosure further provides a detection apparatus including the above-mentioned detection collimation unit and a SPECT imaging system. The detection apparatus and the SPECT imaging system have the same technical effect as that of the above-mentioned detection collimation unit, which will not be repeated here.

BRIEF DESCRIPTION OF THE DRAWINGS

The accompanying drawings of the present disclosure are only used for better understanding of the technical solution and advantages of the present disclosure and do not constitute any limitation to the present disclosure, wherein.

DETAILED DESCRIPTION OF EMBODIMENTS

The present disclosure will be further described in detail and completely in combination with specific embodiments. The following descriptions are only exemplary in essence and are not intended to limit the present disclosure, application or use.

Figure 1:
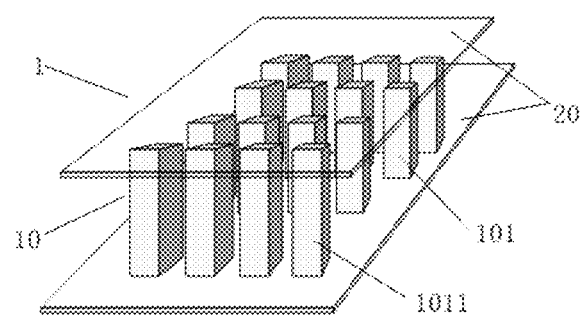
FIG. 1 shows a structural schematic diagram of a detection collimation unit according to an embodiment of the present disclosure.
Figure 2:
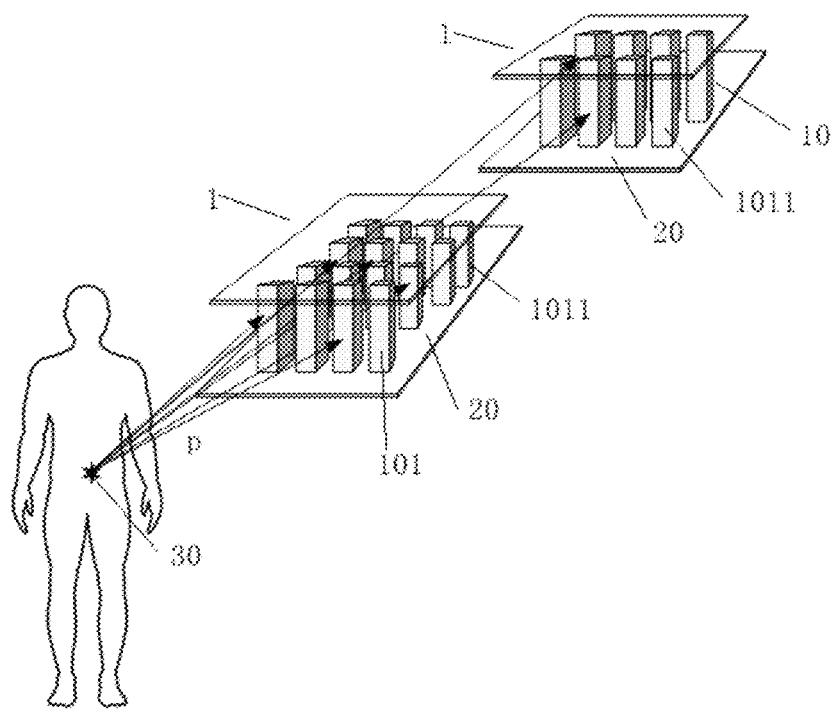
FIG. 2 shows a diagram illustrating a principle of a gamma photon in a human body passing through two detection collimation units according to an embodiment of the present disclosure.

FIG. 1 shows a structural schematic diagram of a detection collimation unit according to an embodiment of the present disclosure. FIG. 2 shows a diagram illustrating a principle of a gamma photon in a human body passing through two detection collimation units according to an embodiment of the present disclosure. As shown in FIG. 1 and FIG. 2, a detection collimation unit 1 according to embodiments of the present disclosure may be applied to a SPECT imaging device or system, and includes: a scintillation crystal array 10 and a number of photoelectric devices 20. The scintillation crystal array 10 is used to receive a gamma photon emitted by a radioactive source in a detected object 30. The number of photoelectric devices 20 are used to receive the gamma photon and convert the gamma photon into a digital signal. Most of the above-mentioned detected objects 30 are target organs in a human body or human bodies. Certainly, the detected objects may also be other detected objects.

The scintillation crystal array 10 is a two-dimensional array, including a plurality of scintillation crystals 101. Each scintillation crystal 101 is an independent rectangular scintillation crystal strip 1011. The plurality of scintillation crystal strips 1011 are arranged in parallel and are spaced from each other. Each scintillation crystal strip 1011 has two end faces and four side faces. The side faces of the scintillation crystal 101 may be used for an incidence of a gamma ray p emitted by the radioactive source in the detected object 30, that is, the side faces of the scintillation crystal 101 may be used as incident planes of the gamma ray p emitted by the radioactive source. One or more photoelectric devices 20 are coupled at the same end of all scintillation crystal strips 1011, and one or more photoelectric devices 20 are coupled at the other end of all the scintillation crystal strips 1011.

An existing low-energy (tens of keV to hundreds of keV) nuclide detection unit used in the SPECT device usually couple the photoelectric device to a gamma photon incident plane (or exit plane) of the scintillation crystal, so that the gamma photon, when passing through the gamma photon incident plane, may be easily blocked and attenuated by the photoelectric device as well as a corresponding electronic device and circuit board, thereby causing a loss of the gamma photon and affecting an image quality.

Based on a design of the detection collimation unit of the above-mentioned structure of the present disclosure, the gamma photon emitted by the radioactive source in the detected object 30, when being incident from a side face of the scintillation crystal strip 1011, does not need to pass through the photoelectric device 20 (that is, the photoelectric device 20 is substantially parallel to an incident direction of the gamma ray p emitted by the radioactive source in the detected object 30). In this way, an effect of gamma ray direction collimation and a goal of photon detection are both achieved without affecting the image quality. Furthermore, as compared with an existing imaging system in which a heavy metal collimator that does not allow a ray to pass therethrough is used, the detection collimation unit 1 of the present disclosure may avoid a loss of the gamma photon and greatly improve a detection efficiency of the gamma photon, without affecting the imaging quality of the SPECT imaging system. At the same time, a process difficulty in processing a plurality of small parallel holes or pinholes in the heavy metal collimator may be avoided, and the processing may be simplified.

As shown in FIG. 1 and FIG. 2, an arrangement method of the scintillation crystal array 10 in the present disclosure is not limited. The scintillation crystal array 10 may be arranged as a two-dimensional arrangement array including a plurality of scintillation crystals 101 arranged in the incident direction of the gamma ray p emitted by the radioactive source, and a plurality of scintillation crystals 101 arranged perpendicular to the incident direction of the gamma ray p emitted by the radioactive source, or as another two-dimensional arrangement array.

Figure 3:
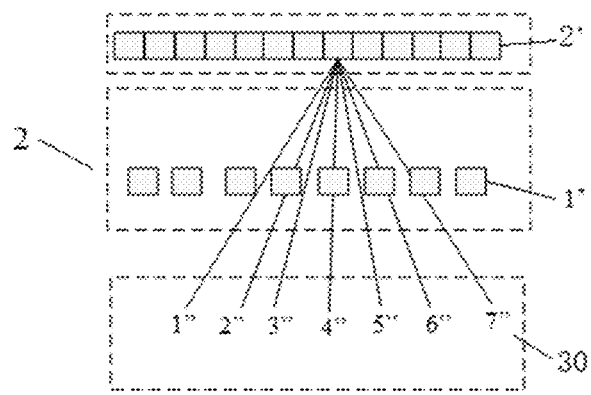
FIG. 3 shows a structural schematic diagram of a detection apparatus according to a first embodiment of the present disclosure.

As shown in FIG. 3, a first embodiment of the present disclosure provides a detection apparatus. The detection apparatus 2 in the first embodiment includes a detection collimation unit 1' (since the detection collimation unit 1' is close to the detected object 30, the detection collimation unit 1' may be used as a detection collimation unit front layer) composed of a row of detection crystals (each detection crystal includes the scintillation crystal strip 1011 and the coupled photoelectric device 20) arranged at intervals and a detection collimation unit 2' (since the detection collimation unit 2' is far from the detected object 30, the detection collimation unit 2' may be used as a detection collimation unit back layer) composed of a row of detection crystals arranged closely. Due to an existence of the detection collimation unit 1', a gamma photon that may be detected at a position of the detection collimation unit 2' has different probabilities to come from different positions 1" to 7" in the human body. The gamma photon has a high probability to come from positions 3" and 5", and a low probability to come from positions 1", 2", 4", 6' and 7". Due to the existence of the detection collimation unit 1' in the embodiment, the detection collimation unit 2' may have a resolution capability and a collimation effect for the incident direction of the gamma photon.

A design of the detection collimation unit layer may affect a detection collimation unit back layer in terms of the detection efficiency and the resolution capability for the incident direction of the gamma photon. A smaller arrangement gap of a crystal array on the detection collimation unit front layer leads to a better resolution capability for the incident direction of the gamma photon on the detection collimation unit back layer, and a lower detection efficiency. A greater thickness of a crystal on the detection collimation unit front layer in the incident direction of the photon leads to a better resolution capability for the incident direction of the gamma photon on the detection collimation unit back layer, and a lower the detection efficiency. FIG. 3 shows an example of a cross section of a region of scintillation crystals 101, in which the scintillation crystal strips 101 are arranged in an axial direction of the human body. By adjusting a spacing of the crystals in the detection collimation unit 1', a collimation effect on the crystals in the detection collimation unit 2' may be changed and a resolution capability of the crystals in the detection collimation unit 2' for the incident direction of the gamma photon may be adjusted.

Figure 4:
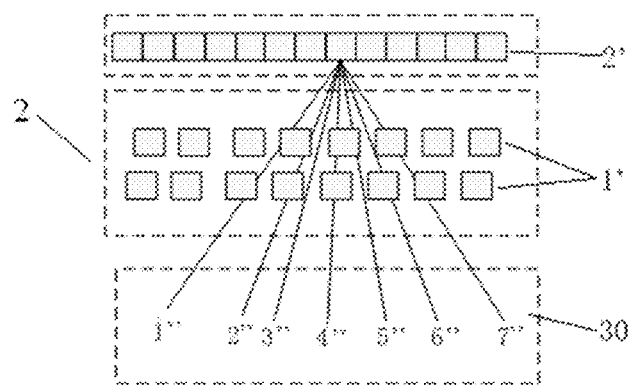
FIG. 4 shows a structural schematic diagram of a detection apparatus according to a second embodiment of the present disclosure.

As shown in FIG. 4, a second embodiment of the present disclosure provides a detection apparatus. The detection apparatus 2 in the second embodiment includes two detection collimation unit layers (equivalent to including the detection collimation unit front layer composed of two rows of interlaced detection crystals and the detection collimation unit back layer composed of a row of closely connected detection crystals). In the embodiment, due to the effect of multi rows of crystals of the detection collimation unit 1' and the detection collimation unit 2', a probability that the photon comes from the position 3" is higher than a probability that the photon comes from other positions. That is, compared with the first embodiment, the detection collimation unit back layer has a better resolution capacity for the incident direction of the gamma photon, but a relatively lower detection efficiency. However, the detection efficiency of the detection collimation unit front layer becomes larger, so a total detection efficiency of the detection apparatus does not become smaller. Moreover, a row of detection crystals at a near end of the detection collimation unit 1' in the detection collimation unit front layer also plays a role of photon detection collimation on a row of detection crystals at a far end of the detection collimation unit 1'.

In an embodiment of the present disclosure, when arranging the plurality of scintillation crystals 101 of the scintillation crystal array 10, sometimes the plurality of scintillation crystals 101 may not be completely arranged in parallel, as long as the plurality of scintillation crystals 101 are substantially parallel, that is, some scintillation crystals 101 may be arranged obliquely, so that a slightly small angle of inclination may be formed between the scintillation crystals 101 and other scintillation crystals 101. For example, the angle of inclination may any value within a range of 0° to 15°.

Figure 5:
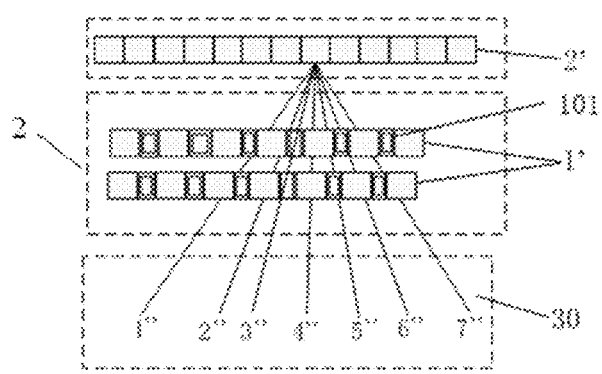
FIG. 5 shows a structural schematic diagram of a detection apparatus according to a third embodiment of the present disclosure.

As shown in FIG. 5, a third embodiment of the present disclosure provides a detection apparatus. In the scintillation crystal array 10 contained in the detection apparatus of the third embodiment, in addition to air, a low-density lightweight material filler may be filled between the scintillation crystals 101 arranged at intervals, so as to stabilize the scintillation crystal 101. Optionally, the material of the filler includes at least one of resin, polyethylene plastic and organic glass. Further, on the premise of ensuring a stability of a structure of the scintillation crystal array 10, a hollow design may be adopted or a size of the filler may be changed, so as to reduce an attenuation of the gamma photon.

In another embodiment of the present disclosure, in the scintillation crystal array 10, a high-density heavy metal material may be filled between the scintillation crystals 101 arranged at intervals, so that the high-density heavy metal material may have a attenuation coefficient significantly different from an attenuation coefficient of the scintillation crystal 101 material to the gamma photon. That is, when the SPECT imaging device has the plurality of detection collimation units arranged at intervals in the incident direction of the gamma ray p emitted by the radioactive source, a probability that the gamma photon passes through the scintillation crystal strip 1011 region of the near-end detection collimation unit to reach the far-end detection collimation unit is significantly different from a probability that the gamma photon passes through a filler region of the near-end detection collimation unit to reach the far-end detection collimation unit. In this way, probabilities that the gamma photon detected on the far-end detection collimation unit come from different directions may be significantly different, so that a collimation effect of the near-end detection collimation unit on the far-end detection collimation unit may be enhanced. The near-end detection collimation unit and the far-end detection collimation unit here belong to relative concepts. Specifically, taking the detected object 30 as a reference, a detection collimation unit close to the detected object 30 is called the near-end detection collimation unit, and a detection collimation unit far away from the detected object 30 is called the far-end detection collimation unit.

Figure 6:
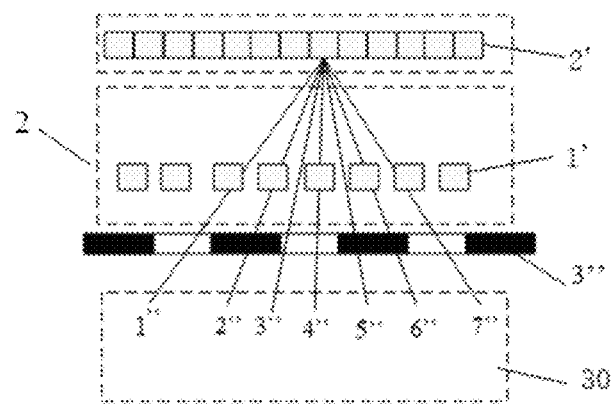
FIG. 6 shows a structural schematic diagram of a detection apparatus according to a fourth embodiment of the present disclosure.

As shown in FIG. 6, a fourth embodiment of the present disclosure provides a detection apparatus. In order to enhance the collimation effect, a heavy metal collimator 3' with an opening may be added between the first detection apparatus 2 (that is, the detection collimation unit 1' in FIG. 6) close to the detected object 30 and the detected object 30, and/or, a heavy metal collimator 3' with an opening is added between two adjacent detection apparatuses 2 (that is, between the detection collimation unit 1' and the detection collimation unit 2' in FIG. 6) in the incident direction of the gamma ray p emitted by the radioactive source, and/or, a heavy metal collimator 3' with an opening is added between (inside the detection apparatus containing the plurality of detection collimation unit layers, and between any two detection collimation unit layers) the detection collimation unit layers of each detection apparatus 2. In addition, the added heavy metal collimator 3' may also enhance a spatial resolution effect of a rear-end detection collimation unit.

Further, in order to ensure a certain detection efficiency, a photon transmittance of the heavy metal collimator 3' needs to be greater than 1%. That is, among photons incident on a front surface of the heavy metal collimator 3', a proportion of photons that may pass through the collimator and be emitted from a rear surface of the heavy metal collimator 3' is greater than 1%. The opening on the heavy metal collimator 3' may be any of a line slot hole, a square hole, a round hole, a tapered hole, etc.

Figure 7:
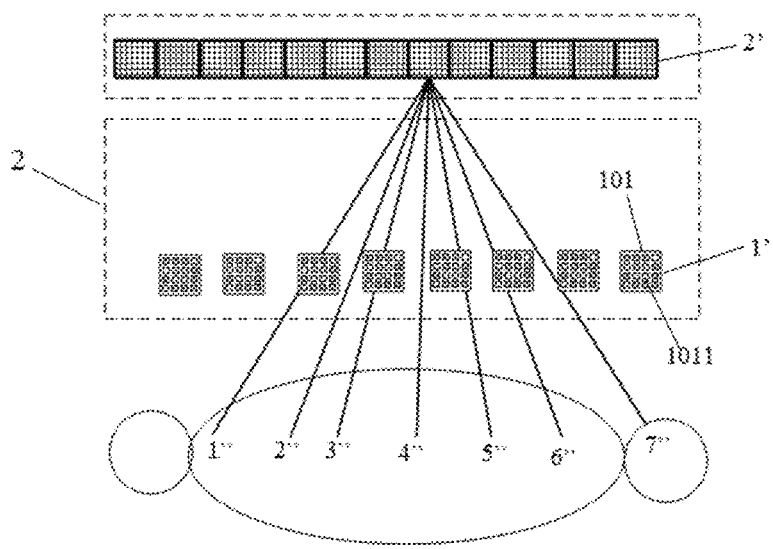
FIG. 7 shows a structural schematic diagram of a detection apparatus according to a fifth embodiment of the present disclosure.
Figure 8:
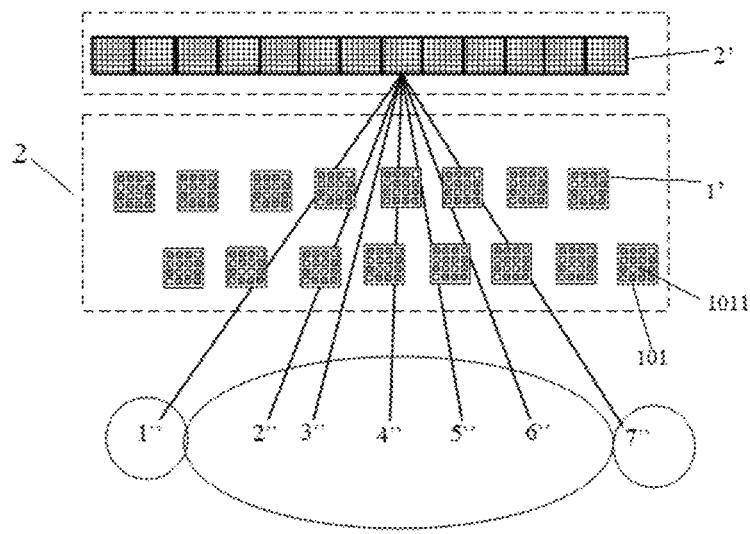
FIG. 8 shows a structural schematic diagram of a detection apparatus according to a sixth embodiment of the present disclosure.
Figure 9:
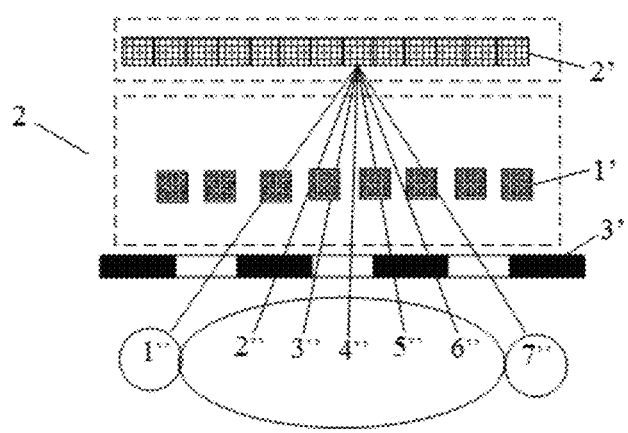
FIG. 9 shows a structural schematic diagram of a detection apparatus according to a seventh embodiment of the present disclosure.

As shown in FIG. 7 to FIG. 9, each of the fifth, sixth and seventh embodiments of the present disclosure provides a detection apparatus, which is different from a structure of the scintillation crystal array 10 of the above-mentioned embodiments (each scintillation crystal 101 is an independent scintillation crystal strip 1011). In the scintillation crystal array 10 of the three embodiments, each scintillation crystal 101 includes the plurality of scintillation crystal strips 1011 spliced together by an adhesive. Of course, in other embodiments of the present disclosure, it is also possible for each scintillation crystal 101 to include an independent scintillation crystal strip 1011 and the plurality of scintillation crystal strips 1011 spliced together.

As shown in FIG. 9, the detection apparatus 2 provided by the seventh embodiment of the present disclosure includes a heavy metal detection collimation unit 3' with a 50% porosity and a detection collimation unit 1' which are arranged as a detection collimation unit front layer, and a detection collimation unit 2' which is used as a detection collimation unit back layer.

Due to an existence of the heavy metal detection collimation unit 3' and the detection collimation unit 1', a gamma photon detected on the detection collimation unit 2' has different probabilities to come from different positions of 1" to 7" in the human body. In the embodiment, a probability that the photon comes from a position 3" is higher, and a probability that the photon comes from other positions is lower. That is, compared with the first embodiment, the detection collimation unit back layer has a better resolution capability for the incident direction of the gamma photon, and a relatively lower detection efficiency. Compared with the fifth embodiment, due to the existence of the heavy metal detection collimation unit 3', a total detection efficiency of the detection apparatus 2 becomes smaller. However, the heavy metal detection collimation unit 3' also plays a role of collimation on a row of detection crystals of the detection collimation unit 1', so the detection apparatus 2 has a better resolution capacity for the incident direction of the gamma photon.

In an embodiment of the present disclosure, a shape of the scintillation crystal strip 1011 is not limited to a cuboid, and may be a cylinder or other forms of strips. The present disclosure may assemble the scintillation crystal matrix 10 by using the scintillation crystal strips 1011 of any one or more shapes of the cuboid, the cylinder and other forms of strips.

In an embodiment of the present disclosure, the manner in which the plurality of photoelectric devices 20 are coupled with the end faces of the plurality of scintillation crystal strips 1011 is not limited, as long as at least one end face of the scintillation crystal strip 1011 is coupled with the photoelectric device 20. It is possible that all photoelectric devices 20 are coupled to the end faces at the same end of all the scintillation crystal strips 1011, and the other end of all the scintillation crystal strips 1011 is a free end. It is possible to adopt the coupling manner as shown in the first embodiment, that is, some of photoelectric devices 20 are coupled to the end faces at the same end of all the scintillation crystals 101, and the remaining photoelectric devices 20 are coupled to the end faces at the other end of all the scintillation crystals 101. It is also possible that some of the photoelectric devices 20 are coupled to the end faces at the same end of a portion of the scintillation crystals 101, and the remaining photoelectric devices 20 are coupled to the end face at the other end of at least one of the portion of the scintillation crystal 101 and to the end face at the other end of the remaining scintillation crystals 101 other than the portion of the scintillation crystal 101, etc.

In the first embodiment, output signals of two photoelectric devices 20 coupled at both ends of all the scintillation crystals 101 are jointly used to calculate and determine a three-dimensional space position where a gamma photon event is applied in the detection collimation unit 1, so that the SPECT imaging device or system may achieve a three-dimensional imaging. The specific calculation formula is as follows:

$$DOI = k \cdot \frac{E_1 - E_2}{E_1 + E_2} + b$$

In the formula, DOI represents a three-dimensional space position where the gamma photon event is applied; $E_1$ and $E_2$ represent signal amplitudes or areas of the photoelectric devices coupled at both ends; k and b are fitting coefficients, which are obtained through a calibration measurement experiment and fitting. The specific calibration process is as follows.
1) A collimated radioactive source is placed on one side of the detection collimation unit, and a DOI position at which the collimated radioactive source incidents on the detection collimation unit is determined.
2) A plurality of events are collected, and $E_1$ and $E_2$ values for each event is obtained.
3)

$$\frac{E_1 - E_2}{E_1 + E_2}$$

is calculated for each event.
4) A polynomial linear fitting is performed according to the DOI value and the $$\frac{E_1 - E_2}{E_1 + E_2}$$

value, to obtain the fitting coefficients k and b.

In an embodiment of the present disclosure, a material of the scintillation crystal strip 1011 may be selected from any one of NaI, CsI, LaBr3, CLYC, BGO, LSO, LYSO, GSO, YSO, YAP, GAGG. Certainly, the plurality of scintillation crystal strips 1011 of the scintillation crystal array 10 may be made of the same material or different materials. Scintillation crystal strips 1011 made of different materials may have different attenuation ratios to the gamma photon. A length of the scintillation crystal strip 1011 is not limited, and may be reasonably selected according to an actual application.

In an embodiment of the present disclosure, at least one of an avalanche photodiode APD, a silicon photomultiplier SiPM, a photomultiplier PMT, a Geiger mode avalanche photodiode GAPD, and a solid-state photomultiplier SSPM may be selected for the photoelectric device 20. When the plurality of detection collimation units are arranged at intervals in the incident direction of the gamma ray p emitted by the radioactive source in the detection apparatus, compared with using a PMT device, use of any one of SiPM, APD, GAPD, and SSPM may reduce a distance between the detection collimation units, thereby reducing a size and a space occupation of the detection apparatus or an entire SPECT imaging device.

Figure 10:
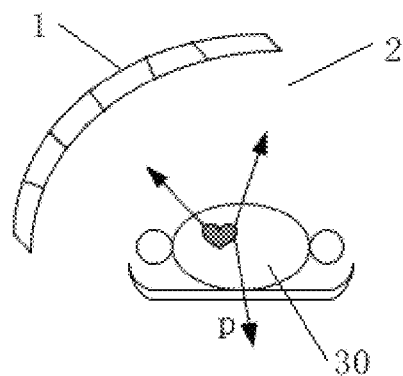
FIG. 10 shows a structural schematic diagram of a detection collimation unit layer in a shape of arc according to an embodiment of the present disclosure.

FIG. 10 shows a structural schematic diagram of a detection collimation unit layer in a shape of arc according to an embodiment of the present disclosure. As shown in FIG. 10, the detection apparatus 2 according to embodiments of the present disclosure includes the plurality of detection collimation units 1 of any type described above. The plurality of detection collimation units 1 are fixedly connected to form a detection collimation unit layer distributed in a shape of arc around the detected object 20.

In another embodiment of the present disclosure, the detection apparatus 2 may include a plurality of detection collimation unit layers arranged at intervals in the incident direction of the gamma ray p emitted by the radioactive source, and the plurality of detection collimation unit layers are staggered, so that at least one scintillation crystal 101 exists on the detection collimation unit 1 of the last detection collimation unit layer. In this way, a gamma photon emitted from a point of an imaging field of view does not pass through any photoelectric device or circuit board material in a transmission path along which the gamma photon is incident and reaches the scintillation crystal of the last detection collimation unit layer. In this way, when the gamma photon is incident on the side face of the scintillation crystal strip 1011 of the scintillation crystal array, a loss of the gamma photon may be avoided without affecting an image quality.

In embodiments of the present disclosure, the implementation of the fixed connection between the plurality of detection collimation units 1 forming the same detection collimation unit layer is not limited, for example, the connection may be implemented by an adhesive or fixed connector.

Figure 11:
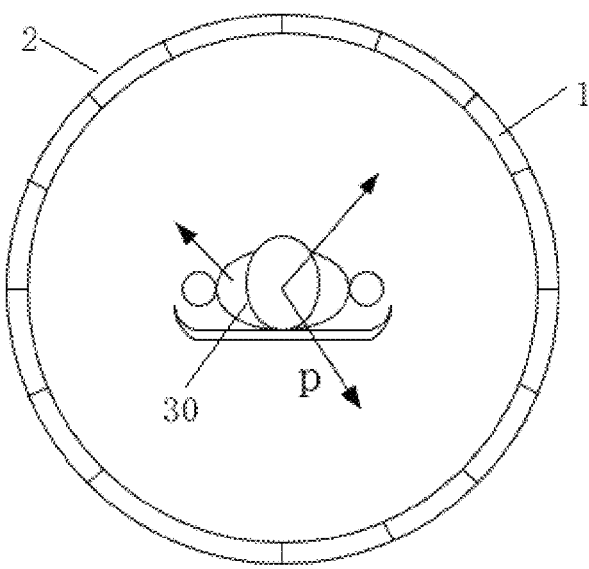
FIG. 11 shows a structural schematic diagram of a detection collimation unit layer in a shape of circular according to an embodiment of the present disclosure.
Figure 12:
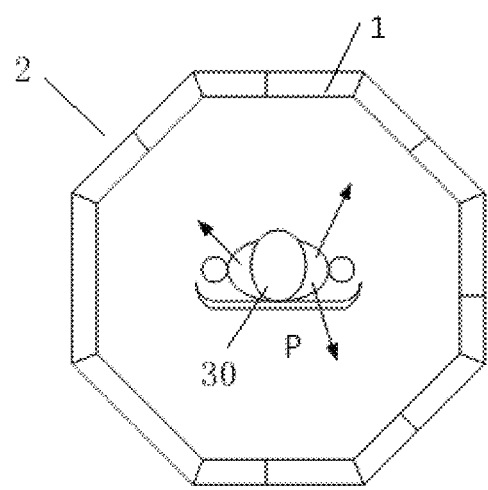
FIG. 12 shows a structural schematic diagram of a detection collimation unit layer in a shape of regular octagon according to an embodiment of the present disclosure.

In embodiments of the present disclosure, a shape in which the plurality of fixedly connected detection collimation units 1 are distributed around the detected object 30 (that is, a shape in which the detection collimation unit layer is formed) is not limited to an arc, but may also be any one of a circular (see FIG. 11), a polygon (for example, a regular hexagon or octagon, see FIG. 12) and a partial polygon (that is, a local shape of the polygon, for example, a half shape of the regular hexagon or octagon).

Figure 13:
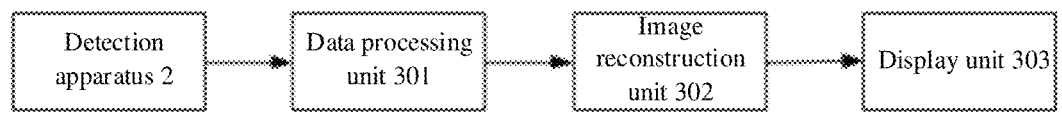
FIG. 13 shows a block diagram of a SPECT imaging system according to an embodiment of the present disclosure.
Figure 14:
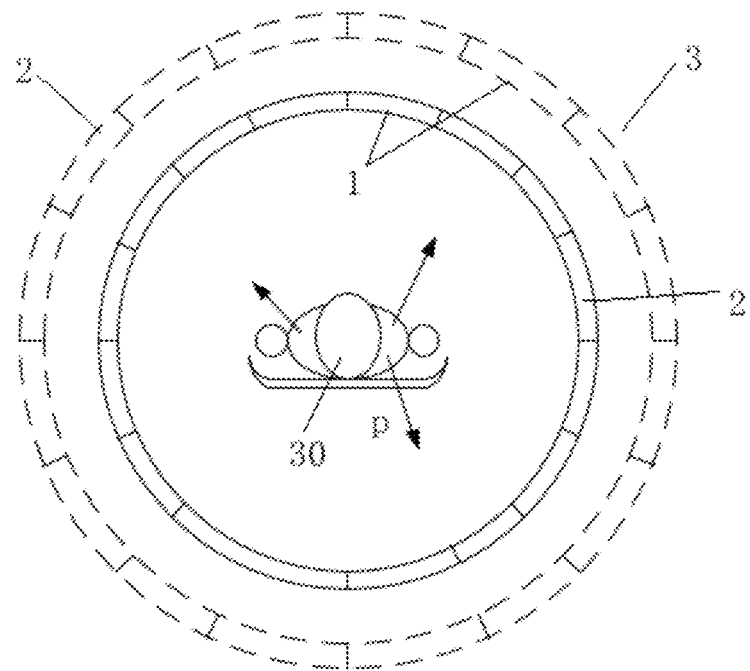
FIG. 14 shows a structural schematic diagram of a SPECT imaging system according to an embodiment of the present disclosure.

FIG. 13 shows a block diagram of a SPECT imaging system according to an embodiment of the present disclosure. FIG. 14 shows a structural schematic diagram of a SPECT imaging system including two detection collimation unit layers according to an embodiment of the present disclosure. As shown in FIG. 13 and FIG. 14, a SPECT imaging system 3 according to embodiments of the present disclosure includes the detection apparatus 2 having two detection collimation unit layers, a data processing unit 301, an image reconstruction unit 302, and a display unit 303. Certainly, in embodiments of the present disclosure, the specific number and structure of the detection collimation unit layers constituting the detection apparatus 2 may be designed according to an actual application.

In an embodiment of the present disclosure, each detection collimation unit layer of the detection apparatus 2 is selectively rotatable around the detected object 30, for example, along a circumference of the detected object 30. Certainly, the present disclosure is not limited to this. Therefore, a flexibility of the system may be improved, and a detection of the detected objects 30 with different sizes and different structures may be facilitated. Further, in order to further improve the flexibility of use of the system, the plurality of detection collimation unit layers may rotate around the detected object 30 at the same speed and direction or at different speeds and directions.

In another embodiment of the present disclosure, the SPECT imaging system 3 includes at least two detection apparatuses 2. Two adjacent detection apparatuses 2 are arranged in the incident direction of the gamma ray p emitted by the radioactive source and are spaced from each other. In the incident direction of the gamma ray p emitted by the radioactive source, a far-end detection apparatus away from the detected object 30 is used to receive a gamma photon which is emitted by the radioactive source in the detected object 30 and passes through one or more near-end detection apparatuses, and convert the gamma photon into the digital signal.

In an embodiment of the present disclosure, a relative position of each detection apparatus in the SPECT imaging system 3, a spacing between two adjacent detection apparatuses 2, a number of scintillation crystal strips 1011 in each detection collimation unit 1, a size of the scintillation crystal strip 1011, and an arrangement mode parameter of the scintillation crystal strip 1011 may be selected according to a spatial resolution and an image signal-to-noise ratio required by the SPECT imaging system 3.

The selection of the above-mentioned parameters requires a compromise between the spatial resolution and the image signal-to-noise ratio characteristics of the imaging system. A final physical structure of the SPECT imaging system may be determined by optimally calculating through the following steps.

1) An imaging field of view region is divided into discrete image pixel units, and a system transmission matrix $A=\{a_{ij}\}$ is calculated according to a group of system design parameter values, where $a_{ij}$ represents a probability that a photon emitted from an image pixel unit j in the imaging system is detected by a scintillation crystal strip i.

2) A uniform image vector f all over the field of view is defined. That is, if an i-th element in the vector f falls within the field of view, a value is 1, otherwise the value is zero. A desired value of projection data obtained from a measurement of f by the imaging system is calculated:

$y = A \cdot f$ where [·] is an operation of multiplying a matrix with a vector. Assuming the system has I detector units and J image units, A is a matrix of I rows×J columns, f is a column vector of 1 row×J columns, y is a column vector of 1 row×I columns.

A Fisher information matrix F is calculated:

$$F = A' \cdot \text{diag}\left[\frac{1}{y}\right] \cdot A$$

where A' is a transpose of A, and $$\text{diag}\left[\frac{1}{y}\right]$$

is a diagonal matrix of I rows×I columns, in which elements on a non-diagonal line are 0, and an element value in an i-th row and an i-th column is a reciprocal of an element value in the i-th column of y.

3) A local shock response matrix of the system is calculated:

$$LIR = F^+ \cdot F$$

where $F^+$ is a Moore-Penrose generalized inverse matrix of F, and LIR is a matrix of J rows×J columns J values in the j-th (j=1, . . . , J) column represent: image vector values output by the imaging system as a response when an impact input is given to the j-th image pixel unit in a field of view space. Ideally, among the J values in the j-th column, only a value in the j-th row is 1, and the other values are 0. At this time, the imaging system has a best spatial resolution. When the spatial resolution of the imaging system is limited, the value in the j-th row and the i-th column is a positive integer between 0 and 1. The smaller the value, the wider an impact response distribution of the imaging system, which represents the poorer spatial resolution of the imaging system.

4) A value of a j-th element of LIR on the diagonal is marked as $R_j$, which represents a spatial resolution characteristic of the imaging system on the j-th pixel unit.

5) Values of LIR on various image pixel units are traversed, and an average is calculated:

$$R = \sum_{j=1}^{J} R_j,$$

in which R is used as an evaluation index of the spatial resolution characteristic of imaging system.

6) A covariance matrix is calculated:

$$COV = F^+ \cdot F \cdot F^+$$

where COV is a matrix of J rows×J columns. The j-th element on the diagonal, i.e., a value in the j-th (j=1, . . . , J) row and the j-th (j=1, . . . , J) column of COV represents: a statistical fluctuation variance of the j-th image pixel unit, which represents a sensitivity of the imaging system to noise. The smaller the value, the lower the sensitivity of the imaging system to noise in measurement data, and the better an image quality.

6) A value of the j-th element of COV on the diagonal is marked as $V_j$, which represents a variance of the j-th pixel unit.

7) Values of COV on various image pixel units are traversed, and an average is calculated:

$$V = \sum_{j=1}^{J} V_j,$$

in which V is used as an evaluation index of the sensitivity of the imaging system to noise in the measurement data.

8) Steps 1) to 7) are repeated by using different design parameter values. The R value and V value are comprehensively compared, and a system design parameter combination with a relatively large R value and a relatively small V value is output as an optimized design result of a system structure.

The data processing unit 301 of the embodiment is used to receive and process a digital signal output by the plurality of detection apparatuses 2, so as to obtain an incident information of each incident gamma photon; information data of each incident gamma photon obtained by the data processing unit 301 includes a position, an energy, time and other data of each incident gamma photon.

The image reconstruction unit 302 of the embodiment is used to receive and process the incident information of a plurality of incident gamma photons output by the data processing unit 301, so as to obtain a distribution information of a radioactive source in the detected object 30 and form a digital image.

Further, the image reconstruction unit 302 may obtain the distribution information of the radioactive source in the detected object by using an analytical reconstruction algorithm, an algebraic iterative algorithm, or a statistical iterative reconstruction algorithm.

The analytic reconstruction algorithm, such as a filtered back projection formula, is as follows:

$$f(x,y) = \int_0^\pi \int_{-\infty}^{\infty} P(\omega,\theta) e^{j2\pi(x \cos \theta + y \sin \theta)} |\omega| d\omega d\theta$$

where f(x,y) is a reconstructed image, $P(\omega,\theta)$ is a one-dimensional Fourier transform of an image projection, and Id is a high-pass filter.

The algebraic iteration algorithm formula is as follows:

$$f^{k+1} = f^k + \lambda^k \frac{p - Cf^k}{\|C\|^2} C^T$$

where $f^k$ is an image of a k-th iteration, $f^{k+1}$ is an image of a (k+1)-th iteration, C is an iterative system transmission matrix, which represents a contribution of a pixel on the image to a projection, and $\lambda^k$ is a relaxation factor of the k-th iteration.

The statistical iterative reconstruction algorithm formula is as follows:

$$f_j^{k+1} = \frac{f_j^k}{\sum_{i=1}^{m} c_{ij}} \sum_{i=1}^{m} c_{ij} \frac{p_i}{\sum_{j=1}^{n} f_j^k c_{ij}}$$

where $f_j^k$ represents a pixel value of a j-th pixel on the image at the k-th iteration, and $c_{ij}$ is a value on the i-th row and the j-th column of the system transmission matrix, which represents a contribution of the j-th point on the image to an i-th detection unit; $f_j^{k+1}$ represents a pixel value of the j-th pixel on the image at the (k+1)-th iteration, and $c_{ij}$ is the value in the i-th row and the j-th column of the system transmission matrix, which represents the contribution of the j-th point on the image to an i-th detection unit.

The display unit 303 of the embodiment is used to receive and display the digitized image formed by the image reconstruction unit 302.

In addition, embodiments of the present disclosure further provide an imaging method to which any of the above-mentioned SPECT imaging systems is applied. The imaging method includes:

receiving a gamma photon emitted by a radioactive source in a detected object and converting the gamma photon into a digital signal;

receiving and processing the digital signal to obtain an incident information of each incident gamma photon;

receiving and processing the incident information of a plurality of incident gamma photons, so as to obtain a distribution information of the radioactive source in the detected object and form a digital image; and receiving and displaying the digital image formed by the image reconstruction unit 302.

In an embodiment of the present disclosure, the plurality of detection apparatuses 2 including one or more detection collimation unit layers may receive the gamma photon emitted by the radioactive source in the detected object 30 and convert the gamma photon into the digital signal. The data processing unit 301 may receive the digital signals output by the plurality of detection apparatuses 2 and process the digital signals one by one to obtain a position, an energy, time and other information of each incident gamma photon. The image reconstruction unit 302 may receive the position, the energy, the time and other information of the plurality of gamma photons output by the data processing unit 301 within a unit time, and determine a solution by an image reconstruction algorithm (for example, an analytical reconstruction algorithm, an algebraic iterative algorithm or a statistical iterative reconstruction algorithm), so as to obtain the distribution information of the radioactive source in the detected object 30 and form the digital image. The display unit 303 is used to finally display the digitized image formed by the image reconstruction unit 302.

Embodiments of the present disclosure further provide a computer-readable storage medium having computer instructions stored thereon, and the computer instructions, when run, execute each step of the above-mentioned imaging method.

Embodiments of the present disclosure further provide a terminal including a memory and a processor. The memory stores computer instructions runnable on the processor, and the processor, when running the computer instructions, executes each step of the above-mentioned imaging method.

In conclusion, the detection collimation unit, the detection apparatus and the SPECT imaging system provided by the present disclosure may achieve an effect of gamma ray direction collimation and a goal of photon detection without affecting an image quality. Furthermore, compared with an existing imaging system in which a heavy metal collimator that does not allow a ray to pass therethrough is used, it is possible to avoid a loss of the gamma photon and greatly improve a detection efficiency of the gamma photon, without affecting an imaging quality of the SPECT imaging system.

At the same time, a difficulty in processing a plurality of small parallel holes or pinholes in the heavy metal collimator may be avoided, and the processing may be simplified.

In addition, by optimally arranging the detector portion in an existing imaging tradition as the detection apparatus of the present disclosure, both a sensitivity and a resolution of the system may be significantly improved.

| Parameter type | GE | Siemens | Philips | The system of the present disclosure |
|---|---|---|---|---|
| Detection efficiency | 18 $s^{-1}/(kBq/cm^2)$ Fan Beam Collimator | 12 $s^{-1}/(kBq/cm^2)$ LEHR Collimator | 12.9 $s^{-1}/(kBq/cm^2)$ LEHR Collimator | 230 $s^{-1}/(kBq/cm^2)$ Multilayer probe collimation unit layer |
| Spatial resolution | 7.5-9.9 mm LEHR Collimator | 8.4-11.7 mm LEHR Collimator | 9.0-10.9 mm LEHR Collimator | 0.5-2 mm |

Through a reasonable design of parameters such as a field of view, a scintillation crystal size, etc., the SPECT imaging system of the present disclosure may greatly improve the detection efficiency (up to 0.1% to 1%) of the gamma photon and the resolution (less than 0.1 mm to 1 mm), compared with the existing imaging system (with a gamma photon detection efficiency of about 0.01%, and a system imaging resolution of about 12 mm) with the heavy metal collimator.

The detection collimation unit of the present disclosure may be used to replace a heavy metal collimator required for a SPECT imaging. This may reduce a loss of the gamma photon, avoid an absorption of the gamma photon by a circuit board and a photoelectric device in the detection collimation unit, and significantly improve a spatial resolution and a detection efficiency of the SPECT imaging. At the same time, a difficulty in a processing a plurality of small parallel holes or pinholes in the heavy metal collimator may be avoided, and the processing may be simplified.

The above-mentioned specific embodiments do not constitute a limitation on the scope of protection of the present disclosure. Those skilled in the art should understand that various modifications, combinations, sub combinations and substitutions may be made depending on design requirements and other factors. Any modifications, equivalent substitutions, improvements, and the like made within the spirit and scope of the present disclosure shall be included in the scope of protection of the present disclosure.

What is claimed is:

1. A detection apparatus comprising a number of detection collimation unit layers with each detection collimation unit layer comprising a number of detection collimation units, wherein the number of detection collimation units in each detection collimation unit layer are fixedly connected and are distributed around a detected object in a shape of any of a circle, a polygon, an arc and a partial polygon;

wherein the number of detection collimation unit layers are arranged in an incident direction of a gamma ray emitted by a radioactive source and are spaced from each other, and the number of detection collimation unit layers are staggered in a direction perpendicular to the incident direction of the gamma ray emitted by the radioactive source, so that at least one scintillation crystal is contained in the detection collimation unit of the last detection collimation unit layer, and a gamma photon emitted from a point of an imaging field does not pass through any photoelectric device or circuit board material in a transmission path along which the gamma photon is incident and reaches the scintillation crystal of the last detection collimation unit layer, wherein each of the number of detection collimation units, comprises: a scintillation crystal array configured to receive the gamma photon emitted by a radioactive source in the detected object; and a number of photoelectric devices configured to receive the gamma photon and convert the gamma photon into a digital signal;

wherein the scintillation crystal array comprises a number of scintillation crystals, the number of scintillation crystals are arranged substantially in parallel and are spaced from each other, and each scintillation crystal has a side face configured to receive a ray emitted by the radioactive source and an end face; and wherein the number of photoelectric devices are coupled to the end faces of the number of scintillation crystals.

2. A SPECT imaging system, comprising the detection apparatus according to claim 1, a data processing unit and an image reconstruction unit;

wherein the data processing unit is configured to receive and process a digital signal output by the detection apparatus, so as to obtain an incident information of each incident gamma photon; and wherein the image reconstruction unit is configured to receive and process the incident information of a plurality of incident gamma photons output by the data processing unit, so as to obtain a distribution information of a radioactive source in a detected object and form a digital image.

3. The SPECT imaging system according to claim 2, wherein each detection collimation unit layer of the detection apparatus is selectively rotatable around the detected object.

4. The SPECT imaging system according to claim 2, wherein the SPECT imaging system comprises at least two detection apparatuses which are arranged in an incident direction of a gamma ray emitted by the radioactive source and are spaced from each other, and in the incident direction of the gamma ray emitted by the radioactive source, a far-end detection apparatus away from the detected object is configured to receive a gamma photon, which is emitted by the radioactive source in the detected object and passes through one or more near- end detection apparatuses, and convert the gamma photon into the digital signal.

5. The SPECT imaging system according to claim 2, wherein a relative position of each detection apparatus in the SPECT imaging system, a spacing between two adjacent detection apparatuses, a number of scintillation crystal strips in each detection collimation unit, a size of the scintillation crystal strip, and an arrangement mode parameter of the scintillation crystal strip are selected according to a spatial resolution and an image signal-to-noise ratio required by the SPECT imaging system.

6. The SPECT imaging system according to claim 2, wherein a heavy metal collimator with an opening is provided between a first detection apparatus close to the detected object and the detected object, and/or between two adjacent detection apparatuses in an incident direction of a gamma ray emitted by the radioactive source, and/or, between the detection collimation unit layers of each detection apparatus.

7. The SPECT imaging system according to claim 6, wherein a photon transmittance of the heavy metal collimator is greater than 1%.

8. The detection collimation unit according to claim 1, wherein the scintillation crystal array is a two-dimensional array, and the scintillation crystal array comprises a number of scintillation crystals arranged in the incident direction of the gamma ray emitted by the radioactive source, and a number of scintillation crystals arranged in the direction perpendicular to the incident direction of the gamma ray emitted by the radioactive source.

9. The detection collimation unit according to claim 1, wherein the scintillation crystal comprises at least one independent scintillation crystal strip and/or a plurality of scintillation crystal strips spliced together.

10. The detection collimation unit according to claim 9, wherein at least one end face of the scintillation crystal strip is coupled with a photoelectric device.

11. The detection collimation unit according to claim 1, wherein in the scintillation crystal array, a filler is provided between the scintillation crystals spaced from each other, and a material of the filler includes at least one of resin, polyethylene plastic, organic glass and heavy metal.

* * * * *